| United States Patent [19] | [11] Patent Number: 4,866,190 |
| Tordeux et al. | [45] Date of Patent: Sep. 12, 1989 |

[54] PROCESS FOR THE PREPARATION OF PERHALOALKANESULFINIC AND -SULFONIC ACIDS, PERHALOALKANESULFINIC AND -SULFONIC ACID SALTS AND OTHER DERIVATIVES OF THESE ACIDS

[75] Inventors: Marc Tordeux, Sceaux; Bernard Langlois, Lyons; Claude Wakselman, Paris, all of France

[73] Assignee: Rhone-Poulenc Chimie, Courbevoie, France

[21] Appl. No.: 152,029

[22] Filed: Feb. 3, 1988

[30] Foreign Application Priority Data

Feb. 4, 1987 [FR] France ................................ 87 01503

[51] Int. Cl.$^4$ ...................... C07C 145/00; C07F 1/08; C07F 3/06
[52] U.S. Cl. .................................. 556/111; 556/119; 562/113; 562/125; 562/829; 562/834
[58] Field of Search ......................... 260/513.7, 513 F; 556/111, 119

[56] References Cited

U.S. PATENT DOCUMENTS 2,732,398 1/1956 Brice et al. ........................... 260/503
4,221,734 9/1980 Commeyras et al. ................ 260/408

FOREIGN PATENT DOCUMENTS 165135 12/1985 European Pat. Off. .

*Primary Examiner*—Nicky Chan
*Attorney, Agent, or Firm*—Finnegan, Henderson, Farabow, Garrett & Dunner

[57] ABSTRACT

A process for the preparation of perhaloalkanesulfinic and -sulfonic acids and derivatives of these acids. A perhaloalkanesulfinic acid salt is prepared by contacting a metal hydroxymethanesulfinate (preferably, a sodium, zinc or copper hydroxymethanesulfinate) with a perhaloalkyl halide group, in a polar solvent. Optionally, the perhaloalkanesulfinic acid salt is then converted to a perhaloalkanesulfinic or -sulfonic acid or a derivative of either of these acids.

8 Claims, No Drawings

PROCESS FOR THE PREPARATION OF PERHALOALKANESULFINIC AND -SULFONIC ACIDS, PERHALOALKANESULFINIC AND -SULFONIC ACID SALTS AND OTHER DERIVATIVES OF THESE ACIDS

FIELD OF THE INVENTION

The present invention relates to a process for the preparation of perhaloalkanesulfinic and -sulfonic acids and their derivatives. More particularly, it relates to the preparation of perfluoroalkanesulfinic and -sulfonic acid salts.

BACKGROUND OF THE INVENTION

Perfluoroalkanesulfonic acids are employed as wetting agents or as surfactants in detergents. They also find utility in the preparation of products having interfacial properties.

The preparation of these compounds by electrofluorination (for example, according to U.S. Pat. No. 2,732,398) is known. A preparation process employing an electrochemical method is ruled out, however, because of its excessively high industrial cost.

Known chemical methods of preparation of these compounds involve the condensation of sulfur dioxide with perfluoroalkylmagnesium derivatives or with perfluoroalkyl halides in the presence of zinc (U.S. Pat. No. 4,221,734). From an industrial safety standpoint, such magnesium-containing derivatives, being far too violent, cannot be used.

Zinc, moreover, disadvantageously gives rise to zinc hydroxide when the reaction medium is treated. The separation of zinc hydroxide on an industrial scale presents serious problems.

DESCRIPTION OF THE INVENTION

A new process has been discovered which enables the disadvantages of the prior art to be overcome, and which is particularly economically advantageous from an industrial standpoint.

The subject of the present invention, which has enabled these objectives to be achieved, is a process for the preparation of a perhaloalkanesulfinic acid salt of formula (I):

$$M[SO_2-R_f]_n \quad (I)$$

wherein $R_f$ represents a polyfluorinated perhaloalkyl group containing at least two carbon atoms and not containing a halogen atom other than fluorine on the carbon atom adjacent to that which carries the $SO_2$ group, M represents a metal, and n is equal to 1 or 2 depending on the valency state of the metal M, comprising the step of contacting a metal hydroxymethanesulfinate of formula (II):

$$M[SO_2CH_2OH]_n \quad (II)$$

wherein M and n have the same meaning as in formula (I), in a polar solvent, with a perhaloalkyl halide of formula: $R_fX$ wherein $R_f$ represents a polyfluorinated perhaloalkyl group containing at least two carbon atoms and not containing a halogen atom other than fluorine on the carbon atom adjacent to that which carries the group X, wherein X represents chlorine, bromine or iodine, for a time sufficient to obtain said perhaloalkanesulfinic acid salt of formula (I). Use of alkali metal hydroxymethanesulfinates is particularly preferred.

The present invention also provides a process for the preparation of a compound selected from the group consisting of a perhaloalkanesulfinic acid, a perhaloalkanesulfonic acid, and a derivative of either of said acids, said compound being converted from a perhaloalkanesulfinic acid salt of formula (I):

$$M[SO_2-R_f]_n \quad (I)$$

wherein $R_f$ represents a polyfluorinated perhaloalkyl group containing at least two carbon atoms and not containing a halogen atom other than fluorine on the carbon atom adjacent to that which carries the $SO_2$ group, M represents a metal, and n is equal to 1 or 2 depending on the valency state of the metal M, comprising the steps of:

(a) contacting a metal hydroxymethanesulfinate of formula (II):

$$M[SO_2CH_2OH]_n \quad (II)$$

wherein M and n have the same meaning as in formula (I), in a polar solvent, with a perhaloalkyl halide of formula: $R_fX$ wherein $R_f$ represents a polyfluorinated perhaloalkyl group containing at least two carbon atoms and not containing a halogen atom other than fluorine on the carbon atom adjacent to that which carries the group X, wherein X represents chlorine, bromine or iodine, for a time sufficient to obtain said perhaloalkanesulfinic acid salt of formula (I); and (b) converting said perhaloalkanesulfinic acid salt of formula (I) to said compound.

In contrast to the prior art mentioned above, and especially in contrast to U.S. Pat. No. 4,221,734, in accordance with the preocess of the present invention, the acids and derivatives of the present invention may be prepared in the substantial absence of a metal catalyst.

Examples of compounds of formula (I) include sodium and potassium salts of perfluorooctanesulfinic acid, pentafluoroethanesulfinic acid, perfluorohexanesulfinic acid and 1,1-dichloro-2,2-2-trifluoroethanesulfinic acid.

Examples of preferred polar solvents include amides such as, in particular, formamide, dimethylformamide, N-methylpyrrolidone and dimethylacetamide, and solvents such as sulfolane. The use of dimethylformamide is particularly preferred.

Examples of metal hydroxymethanesulfinates include, in particular, sodium hydroxymethanesulfinate, sold under the trade name Rongalite®, zinc hydroxymethanesulfinate, sold under the trade name Decroline® and copper hydroxymethanesulfinate.

Examples of particularly preferred polyfluorinated perhaloalkyl halides of the formula $R_fX$ include those containing 2 to 12 carbon atoms.

Among the class of perfluoroalkyl halides, the use of perfluoroalkyl iodides is preferred. Indeed, these compounds are well known for their chemical inertness, and it is particularly surprising that in the presence of hydroxymethanesulfinates they react to form perfluoroalkanesulfinic acid salts.

According to a preferred process for implementing the invention, the metal hydroxymethanesulfinate, particularly an alkali metal hydroxymethanesulfinate, is introduced into the reactor. It is preferable to remove any oxygen present in the reactor, and then to introduce the polyfluorinated perhaloalkyl halide. When the reaction is complete, the reaction solvent or solvents is (are) removed, and the sulfinic acid salt obtained is purified by extraction with solvents such as ethyl acetate.

Derivatives of the sulfinic acid salt may be obtained by methods well-known in the art. For example, the sulfinic acid salt may be converted by oxidation into a sulfonic acid salt in a manner known to the person skilled in the art (for example, by oxidation with oxygenated water). A sulfonic acid may then be obtained, for example, by acidifying the salt with anhydrous sulfuric acid in a manner which is also known to the person skilled in the art. The sulfinic acid salt itself may also be converted directly to a sulfinic acid by such an acidification process.

An oxidation process may be carried out directly by introducing chlorine into the reaction medium containing the sulfinic acid salt, which enables sulfonyl chloride to be obtained.

By methods well-known to those in the art, sulfones may also be obtained from the perhaloalkanesulfinic acid salts of formula (I) of the invention.

It is preferable to work at a reaction temperature ranging from 0° to 85° C. and, more preferably still, at a temperature ranging from 20° to 40° C.

The reactor preferably does not consist of a reactive material (such as those described in the patent application published under EP No. 165,135). The use of a glass reactor is thus preferred.

The perhaloalkanesulfonic acids and their derivatives obtained by the process of the present invention may be employed as catalysts in processes such as alkylation, or as surfactants, especially in detergents.

The following examples illustrate certain embodiments of the invention and should not be regarded as limiting the scope or spirit of the invention.

EXAMPLE 1

PREPARATION OF SODIUM 1,1-DICHLORO-2,2,2-TRIFLUOROETHANESULFINATE 10 ml of dimethylformamide, 3.7 g of sodium hydroxymethanesulfinate and 3.74 g of 1,1,1-trichloro-2,2,2-trifluoroethane were placed in an Erlenmeyer flask. The mixture was stirred for 12 hrs. The degree of conversion into sodium 1,1-dichloro-2,2,2-trifluoroethanesulfinate ($\delta_F = -71$ ppm) was 30% relative to the trichlorotrifluoroethane and 15% relative to the sodium hydroxymethanesulfinate.

EXAMPLE 2

PREPARATION OF PERFLUOROBUTANESULFONYL CHLORIDE 10 ml of dimethylformamide, 2.6 g of sodium hydroxymethanesulfinate and 3.5 g of perfluorobutyl iodide were placed in an Erlenmeyer flask. The mixture was stirred for 12 hours. By $^{19}F$ NMR, it was observed that 66% of the iodide was converted. After filtering, the dimethylformamide was evaporated under vacuum. 20 ml of water were added. The solids were removed by filtration. 1 liter of chlorine was passed through the solution. 1.7 g of perfluorobutanesulfonyl chloride were obtained by decantation. Yield: 53% [82% yield relative to the perfluoroalkyl iodide converted ($\delta_F = -104.6$ ppm; b.p. = 100° C.), yield relative to the sodium hydroxymethanesulfinate: 26%].

EXAMPLE 3

PREPARATION OF PERFLUOROOCTANESULFONYL CHLORIDE (a) Example 2 was repeated, replacing the perfluorobutyl iodide with 5.5 g of perfluorooctyl iodide. 75% of the iodide was converted. After chlorination, 3.2 g of perfluorooctanesulfonyl chloride were obtained. Yield: 62% (82% relative to the perfluorooctyl iodide converted). $\delta_F = -104.6$ ppm; m.p. = 36° C.; b.p. 22 mm Hg = 102° C.

(b) The above experiment was repeated with 3.9 g of zinc hydroxymethanesulfinate. In this case, the perfluorooctyl iodide was completely converted. After chlorination, the yield was 85%, and 42% relative to the zinc hydroxymethanesulfinate.

EXAMPLE 4

PREPARATION OF PERFLUOROOCTANESULFONYL CHLORIDE 10 ml of dimethylformamide, 3.7 g of sodium hydroxymethanesulfinate and 5.5 g of perfluorooctyl iodide were placed in an Erlenmeyer flask. The mixture was stirred for 12 hours. By fluorine nuclear magnetic resonance spectroscopy, it was observed that 81% of the iodide was converted, 24% of which was 1-hydridoperfluorooctane, $C_8F_{17}H$. 5 ml of water were added. Dimethylformamide was extracted with methylene chloride. 1 liter of chlorine was passed through the aqueous solution, and 2.5 g of perfluorooctanesulfonyl chloride were obtained. Yield: 48% (59% relative to the perfluorooctyl iodide converted) and 24% relative to the sodium hydroxymethanesulfinate.

We claim:

1. A process for the preparation of a perhaloalkanesulfinic acid salt of formula (I):

$$M[SO_2-R_f]_n \qquad (I)$$

wherein $R_f$ represents a polyfluorinated perhaloalkyl group containing at least two carbon atoms and not containing a halogen atom other than fluorine on the carbon atom adjacent to that which carries the $SO_2$ group, M represents a metal, and n is equal to 1 or 2 depending on the valency state of the metal M, comprising the step of contacting a metal hydroxymethanesulfinate of formula (II):

$$M[SO_2CH_2OH]_n \qquad (II)$$

wherein M and n have the same meaning as in formula (I), in a polar solvent, with a perhaloalkyl halide of formula: $R_fX$ wherein $R_f$ represents a polyfluorinated perhaloalkyl group containing at least two carbon atoms and not containing a halogen atom other than fluorine on the carbon atom adjacent to that which carries the group X, wherein X represents chlorine, bromine or iodine, for a time sufficient to obtain said perhaloalkanesulfinic acid salt of formula (I).

2. The process of claim 1, wherein said metal hydroxymethanesulfinate of formula (II) is selected from sodium, zinc and copper hydroxymethanesulfinates.

3. The process of claim 1, wherein said polar solvent is dimethylformamide.

4. The process of claim 1, wherein said perhaloalkyl halide of formula $R_fX$ is a perfluoroalkyl iodide.

5. The process of claim 4, wherein said perfluoroalkyl iodide contains from 2 to 12 carbon atoms.

6. The process of claim 1, wherein the reaction temperature ranges from 0° to 85° C.

7. The process of claim 6, wherein said reaction temperature ranges from 20° to 40° C.

8. The process of claim 1, wherein said metal hydroxymethanesulfinate is an alkali metal hydroxymethanesulfinate.

* * * * *